United States Patent [19]

Seib et al.

[11] Patent Number: 4,858,317

[45] Date of Patent: Aug. 22, 1989

[54] STOMA FLANGE CUTTER

[75] Inventors: George E. Seib; Bradley D. Seib, both of Calgary, Canada

[73] Assignee: Geepard Industries, Inc., Calgary, Canada

[21] Appl. No.: 199,177

[22] Filed: May 26, 1988

[51] Int. Cl.4 .............................................. B26B 27/00
[52] U.S. Cl. ......................................... 30/115; 30/123; 30/316
[58] Field of Search ........................ 30/113.1, 115, 123, 30/130, 301, 316; 83/167; 604/388

[56] References Cited

U.S. PATENT DOCUMENTS

| 1,324,586 | 2/1920 | Dragon | 30/316 |
| 3,232,246 | 2/1966 | Mishkian | 30/316 X |
| 4,010,543 | 3/1977 | Nusbaum | 30/316 |
| 4,391,042 | 7/1983 | Senderhand | 30/316 |

Primary Examiner—Douglas D. Watts
Attorney, Agent, or Firm—Arnold, White & Durkee

[57] ABSTRACT

Disclosed is apparatus for cutting a stoma flange comprising a first section and a second section, the first section having a first surface portion with an annular cutter element extending perpendicularly therefrom. A post extends from the surface within the cutter element and is concentric therewith, the cutter element and post each extending in an axial direction a predetermined distance from the first surface portion. The second section has first and second spaced surface portions and a through bore between the surface portions, the bore being adapted for cooperative association with the post. The first surface portions of the sections cooperate to protect the cutter, when the respective first surfaces are in confronting orientation and the post and bore are cooperatively associated. The sections are separable and movable whereby the first surface of the first section and the second surface of the second section are in a confronting orientation with the post and bore in cooperative association whereby the cutter is exposed and adapted to cut a stoma flange in cooperation with the second surface.

9 Claims, 1 Drawing Sheet

U.S. Patent
Aug. 22, 1989
4,858,317
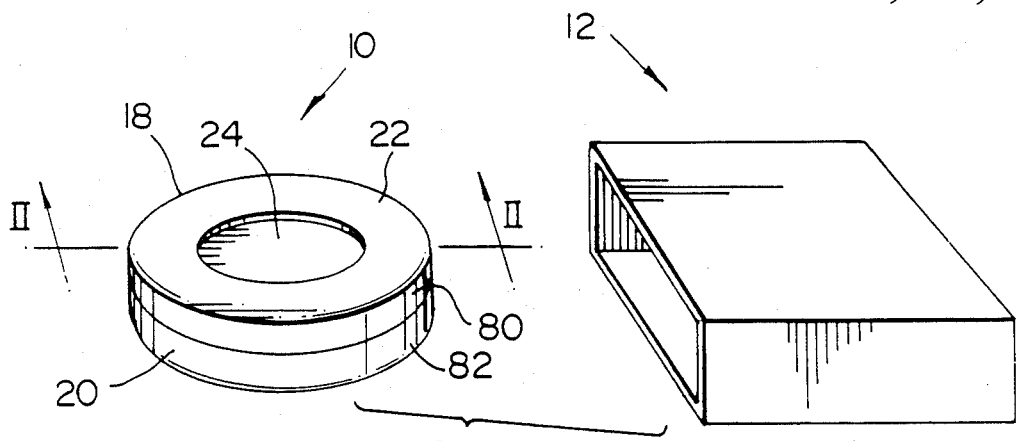
FIG.1
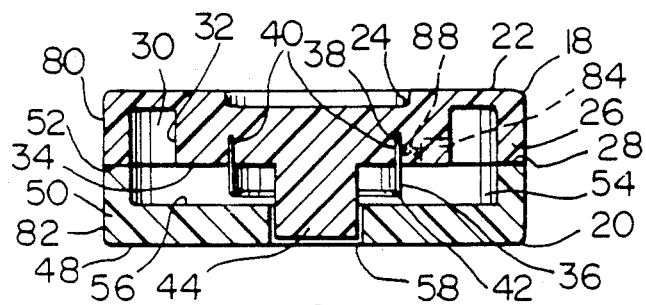
FIG. 2
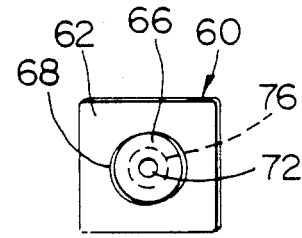
FIG.3A
FIG.3B
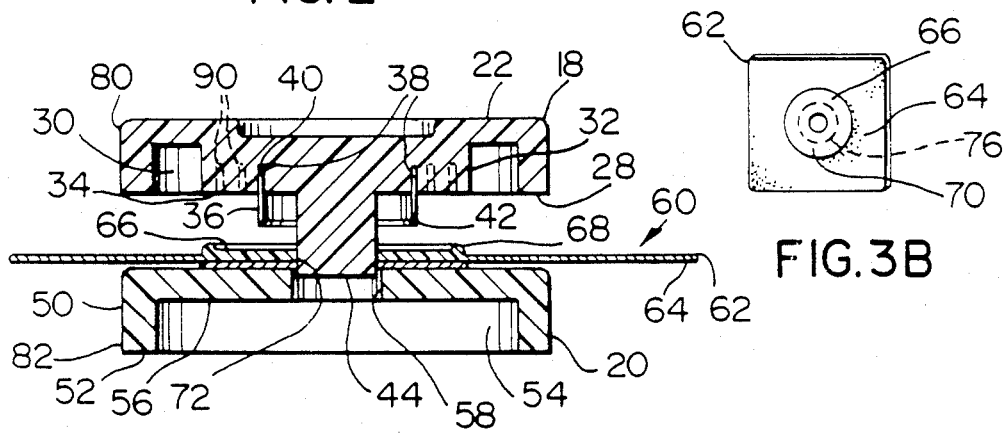
FIG.4

STOMA FLANGE CUTTER

FIELD OF THE INVENTION

The invention relates to a cutter for a flange and more particularly to a device for cutting a preselected sized ostomy or stoma flange.

BACKGROUND OF THE INVENTION

Colostomy is the establishment by surgical means of an artificial opening in the wall of the abdomen through which body waste is discharged directly from the colon instead of passing out through the rectum and anus. A colostomy is performed when part of the colon or rectum is removed due to cancer or when it appears otherwise advisable to bypass the lower colon in order to relieve the condition such as ulcerative colitis.

The collector bag which must be carried by a person who has had a colostomy, requires a sealed connection with the skin about the opening and presently a stoma flange is used which flange is held to the skin by adhesive supplied on the flange that holds the collector bag.

The flange must be changed on a regular basis and patients usually purchase flange material having a predetermined sized hole therein and then cut the flange with scissors or the like to enlarge the hole so that it coincides with their particular body opening. Because of the thickness of the flange and the accuracy required, it has been difficult for users to cut the flange with scissors for their own use. However, it is essential that the flange be cut properly to protect against inflammation and discomfort.

More particularly, stoma flanges are usually sold with about a 10 mm hole therein and exemplary outer dimensions of 100 mm×100 mm. If the flange hole is not enlarged properly to fit the body opening, the flange will leak body fluids, which, in addition to whatever unpleasant smell may be associated, will, because of the acidic nature of the fluids, cause severe irritation of the skin about the flange and body opening. It will be appreciated that removing an adhesive attached flange from the skin alone causes irritation, but to have to do it more frequently because of leakage and fluid irritation, compounds the discomfort to the patient. The cutting of the proper aperture or hole is therefore critical to the comfort of the patient.

It has also been found that the flange material and adhesive backing is such that in flanges where the apertures have been prior cut to size, the effectiveness of at least the material around the opening deteriorates within a couple of days, increasing dramatically the chance of leakage within a short period of use, necessitating more frequent changes of the flange. Thus a patient must keep a supply of uncut flanges and cut them only when the need arises.

Accordingly, there is a need for a device which has been designed and developed to assist ostomy patients themselves to cut the proper hole in the ostomy flange, a device that is easy to use, inexpensive and can be transported without difficulty by the patient.

SUMMARY OF THE INVENTION

Thus this invention seeks to provide a device which is effective to cut the appropriate sized flange for the ostomy patient and a device which is easy to use and is entirely portable.

The invention in one aspect comprehends apparatus for cutting a stoma flange comprising a first section and a second section, the first section having a first surface portion with an annular cutter element extending perpendicularly therefrom. A post also extends from the surface within the cutter element and is concentric therewith, the cutter element and post each extending in an axial direction a predetermined distance from the first surface portion. The second section has first and second spaced surface portions and a through bore between the surface portions, the bore being adapted for telescoping cooperation with the post. Means cooperate between the first surface portion of the two sections when the respective first surfaces of each are in confronting orientation with the post and bore cooperatively associated, to protect the cutter element. The two sections are separable and movable whereby the first surface of the first section and the second surface of the second section are in a confronting orientation with the post and bore in operative association whereby the cutter is exposed and adapted to cut a stoma flange in cooperation with the second surface.

The cooperating means may take the form of opposing rims on the two sections.

Another feature is to provide a plurality of grooves into one of which a selected cutter depending on the demand is press fitted. Alternatively, means such as a screw fastener means could be used to secure the cutter in the appropriate groove, the cutter preferably having both ends sharpened and adapted to flip end-to-end when one end becomes dull.

Other aspects, features and advantages of the invention will become apparent from the detailed description herein of a preferred embodiment.

BRIEF DESCRIPTION OF THE DRAWINGS

FIG. 1 is a perspective view of the cutter device in a closed position but separated from its package or envelope cover.

FIG. 2 is a sectional elevational view of the device taken through line 2—2 of FIG. 1.

FIGS. 3A and 3B are small perspective views, front and back respectively of an ostomy flange as it is retailed for a user.

FIG. 4 is a sectional elevational view of the device but with the device in a cutting mode and showing flange material being cut.

DESCRIPTION OF THE PREFERRED EMBODIMENT

FIG. 1 illustrates the cutter device 10 in an exploded relation relative to the package or envelope cover 12, the dimensions of cover 12 being such that device 12 will slip in and out of cover 12 for storage and transport. Package 12 is squarish in configuration with its lateral dimensions similar to the diametric extent of device 10. Package 12 could be made of cardboard or plastic as desired.

Device 10 is circular in configuration and in FIGS. 1 and 2 is shown in perspective and cross-section in its storage condition. Device 12 comprises top section 18 and bottom section 20. Top section 18 has top surface portion 22 with circular recess 24 therein and annular rim 26 with edge 28, recess 24 simply providing an area for advertising or instructional material. Inwardly of rim 26 is annular recess 30 and central cutter support 32 which has surface 34 generally planar with rim edge 28.

Annular cutter 36 has edge 38 press fitted into a suitable groove 40 in surface 34 and has sharpened edge 42 extending away from surface 34. Inwardly of cutter 36 and extending from surface 34 is cylindrical post 44 which extends further from surface 34 than cutter 36.

Bottom section 20 has outer surface 48 which is of similar diametric extent to top section 18 and has an annular rim 50 with edge 52 similar to rim 26 of top section 20. Inwardly of rim 50 is recess 54 defined by rim 50 and surface 56 which extends across bottom section 20 to meet circular bore 58 which is dimensioned to rotatably fit with post 44.

When not in use, device 10 assumes a configuration as shown in FIG. 2 wherein post 44 fits within bore 58 and rim edges 28 and 52 contact in such manner that sharpened cutter edge 42 is spaced from inner surface 56 of bottom section 20. When device 10, as shown in FIGS. 1 and 2, is slipped into package cover 12, sections 20 and 22 are effectively held together for storage and transportation.

Commercially available stoma flange 60 shown in FIG. 3A (front) and FIG. 3B (back) has peripheral portion 62 with pressure sensitive adhesive backing 64 and a central portion 66 of appropriate flange material capable of properly sealing with the body opening. Central portion 66 includes annular plastic ridge 68 associated with the flange material, which ridge provides means to which the colostomy bag is sealingly connected. The back of central portion 66 also has pressure sensitive adhesive thereon for connection to the skin, the adhesive protected by backing 70. Aperture or hole 72 in central portion 66 and concentric with ridge 64 is of a predetermined size, usually 10 mm in diameter and must be enlarged with scissors or the like to the exact size required by the particular patient's system.

As shown in FIG. 4, the aperture 72 is placed over or in registry with post 44 of top section 18. Bottom section 20 is inverted from its position as shown in FIG. 2 and bore 58 placed in registry with post 44, surface 48 of section 22 confronting section 36. The sections may then be pushed together (one section in each hand) and rotated, if necessary, relative to each other. More particularly, between pressure applied to and slight rotation of annular cutter 36, relative to surface 48, the flange material of central portion 66 is cut so that a flange having an appropriately sized hole 76 (dotted lines in FIG. 3) is provided for its intended use. The depth of the cutter 36 is greater than the height of ridge 68 so the surface 32 does not contact ridge 68.

The outside surface 80, 82 of rims 26 and 50 may be roughened or otherwise treated to provide a non-slip surface.

Cutter 36 is preferably 400 series stainless steel and sections 18 and 20 are injection molded of suitable plastic, such as ABS. Cutter 36 can be press fitted into an appropriate groove 40 as noted above. It should also be apparent that in production, upper section 18 may be molded or formed with more than one groove 40 such as grooves 90 shown in dotted lines in FIG. 4 so that a blade of an appropriate size may be pressfitted into the complementary groove as circumstances and demand dictate.

Further, it should be apparent that in production, with suitable modification of cutter support 32 such as one or more recess(es) 86 shown in FIG. 2 in dotted lines, Allen screw(s) 88 could be used to secure cutter 36 in groove 40 by contacting a side of cutter 36. With this variation, however, the other end of cutter 36 could be sharpened so that the cutter could be flipped "end-to-end" to expose a new sharp edge.

Obviously many other means of securing cutter 36 in groove 40 are possible.

By way of a particular exemplary embodiment, top and bottom sections 18 and 20 are each 70 mm wide by 12 mm thick with post 44, 10 mm in diameter and bore 58, 12 mm in diameter. Cutter support 32 is 45 mm in diameter and cutter 36, depending on the system being used and the size of the body opening required, usually ranges from 19 mm to 38 mm in diameter in increments such as 19 mm, 22 mm, 25 mm, 29 mm, 32 mm and 38 mm. Cutter 36 extends about 5 mm from surface 34 and recess 54 is about 7 mm deep whereby there is about a 2 mm gap between sharpened edge 42 of cutter 36 and surface 56 when the device is in a closed, non-use or storage condition as shown in FIG. 2. In those cases where cutter support 32 is molded or formed with more than one groove (40 and 90) and the selected annular knife is simply press fitted into the appropriate groove, the surface 32 would have a series of three grooves at diameters of either (a) 19, 25 and 32 mm or (b) 22, 29 or 38 mm. This would provide an appropriate array of three grooves on support 32 and yet maintain sufficient material between adjacent grooves for strength purposes.

Further, it will be appreciated that recess 30 serves no purpose other than to lighten top section 18. Provided there is cooperation between a portion of the top 18 and bottom 20 sections to space cutter edge 42 from surface 56, the spacing need not be by rim edges 22 and 52. By way of example, one or the other section need not have a rim provided the other section has some means to space the cutter edge 42 from the confronting surface 56 when the sections 18 and 20 are in storage position (FIG. 2).

Various other modifications will be apparent to those skilled in the art and we include all modifications and variations which fall within the claims appended here.

The embodiments of the invention in which an exclusive property or privilege is claimed are defined as follows:

1. Apparatus for cutting a stoma flange comprising:
 a first section and a second section;
 said first section having a first surface portion with an annular cutter element extending perpendicularly therefrom, a post extending from said surface within said cutter element and concentric therewith, said cutter element and post each extending in an axial direction a predetermined distance from said first surface portion;
 said second section having first and second spaced surface portions and a through bore between said surface portions, said bore being adapted for cooperative association with said post;
 means cooperating between said first surface portions of said sections to protect said cutter, when said respective first surfaces are in confronting orientation and said post and bore are cooperatively associated;
 said sections being separable and movable whereby said first surface of said first section and said second surface of said second section are in a confronting orientation with said post and bore in cooperative association whereby said cutter is exposed and adapted to cut a stoma flange in cooperation with said second surface.

2. The apparatus of claim 1 further including means for retaining said sections together when said cutter is being protected.

3. The apparatus of claim 2 wherein said retaining means comprises open ended envelope means into which said sections can be inserted.

4. The apparatus of claim 1 wherein said first surface portion of said first section has annular groove means; and said annular cutter has an end which is pressfitted into said groove means.

5. The apparatus of claim 4 wherein said first surface portion of said first section is made with a plurality of concentric annular groove means.

6. The apparatus of claim 1 wherein said first surface portion of said first section has annular groove means, and means for detachably securing said cutter within said groove means.

7. The apparatus of claim 6 wherein said first surface portion of said first section has a plurality of concentric annular groove means.

8. The apparatus of claim 1 wherein said cooperating means includes annular rim means on at least one of said sections.

9. The apparatus of claim 8 wherein said cooperating means comprises annular rim means on both sections.

* * * * *